(12) United States Patent
Troutner

(10) Patent No.: US 10,299,954 B2
(45) Date of Patent: May 28, 2019

(54) THERAPEUTIC CUSHIONING PANTS

(71) Applicant: Enma Troutner, Suisun City, CA (US)

(72) Inventor: Enma Troutner, Suisun City, CA (US)

(73) Assignee: Enma Troutner, Suisun City, CA (US)

( * ) Notice: Subject to any disclaimer, the term of this patent is extended or adjusted under 35 U.S.C. 154(b) by 78 days.

(21) Appl. No.: 14/622,712

(22) Filed: Feb. 13, 2015

(65) Prior Publication Data
US 2016/0235134 A1 Aug. 18, 2016

(51) Int. Cl.
A41D 13/05 (2006.01)
A61F 5/02 (2006.01)
A61F 5/01 (2006.01)
A61F 5/32 (2006.01)

(52) U.S. Cl.
CPC .......... *A61F 5/028* (2013.01); *A61F 5/0102* (2013.01); *A61F 5/01* (2013.01); *A61F 5/0193* (2013.01); *A61F 5/32* (2013.01)

(58) Field of Classification Search
CPC ............ A41D 13/1254; A41D 2400/44; A41D 13/0543; A41D 13/0531; A41D 13/065
See application file for complete search history.

(56) References Cited

U.S. PATENT DOCUMENTS

| | | | | |
|---|---|---|---|---|
| 1,512,171 A | * | 10/1924 | Homling ................. | A41B 9/08 2/78.2 |
| 1,641,318 A | * | 9/1927 | Carey ................ | A41D 13/0568 2/22 |
| 2,052,973 A | * | 9/1936 | Furtzaig ............. | A41D 13/0556 182/230 |
| 2,091,560 A | * | 8/1937 | Nash .................. | A41D 13/0543 36/2 R |
| 2,132,117 A | * | 10/1938 | Korolick .................. | A41D 1/06 2/228 |
| 3,508,550 A | * | 4/1970 | Vollrath ................. | A41D 1/088 128/891 |
| 4,486,901 A | * | 12/1984 | Donzis ............... | A41D 13/0153 2/22 |
| 4,561,124 A | * | 12/1985 | Thompson ............. | A41D 1/067 2/227 |
| 4,604,761 A | * | 8/1986 | Wright ..................... | A41D 1/06 2/227 |
| 4,624,679 A | * | 11/1986 | McEntee ................. | C08K 5/005 428/907 |
| 4,651,355 A | * | 3/1987 | White .................... | A41D 27/20 2/247 |

(Continued)

*Primary Examiner* — Richale Quinn
*Assistant Examiner* — Anne Kozak
(74) *Attorney, Agent, or Firm* — Perkins Coie LLP

(57) ABSTRACT

The therapeutic pants include at least one cushion that orients the user's leg(s), hip(s), or lower back in a particular alignment. For example, the cushion may be positioned between the user's legs to align the hips or behind the user's leg to elevate the knee or ankle. The therapeutic pants may include one or more retaining pockets configured to retain one or more cushions. In some embodiments, the cushions are removable from the retaining pockets. In some embodiments, at least one retaining pocket and at least one cushion are positioned along the medial (i.e., inner) side of each pant leg. The pant material that extends vertically along one or both lateral sides of each leg can be detachably secured, allowing the therapeutic pants to be readily and repeatedly equipped and removed.

18 Claims, 13 Drawing Sheets

(56) References Cited

U.S. PATENT DOCUMENTS

| | | | | |
|---|---|---|---|---|
| 4,700,407 A * | 10/1987 | Mattila | A41D 13/015 2/16 |
| 4,914,756 A * | 4/1990 | Grassick | A41D 1/06 2/227 |
| 4,999,854 A * | 3/1991 | Fell | A41B 11/14 2/409 |
| 5,008,962 A * | 4/1991 | Smith | A41D 1/06 2/227 |
| 5,084,914 A * | 2/1992 | Hesch | A41D 13/129 2/227 |
| 5,105,473 A * | 4/1992 | Valtakari | A41D 13/015 2/22 |
| 5,161,257 A * | 11/1992 | Arensdorf | A41D 13/0575 2/22 |
| 5,168,576 A * | 12/1992 | Krent | A41D 13/0156 2/16 |
| 5,241,708 A * | 9/1993 | Rodarmel | A61F 5/3769 2/227 |
| 5,315,716 A * | 5/1994 | Baum | A41D 1/06 2/114 |
| 5,377,693 A * | 1/1995 | Loper | A61F 5/00 128/845 |
| 5,584,072 A * | 12/1996 | Kim | A41D 13/0506 2/22 |
| 5,599,290 A * | 2/1997 | Hayes | A41D 13/0156 2/455 |
| 5,636,377 A * | 6/1997 | Wiener | A41D 13/015 2/2.5 |
| 5,658,246 A * | 8/1997 | Saca | A41D 13/015 2/455 |
| 5,664,271 A * | 9/1997 | Bellavance | A47C 20/021 5/630 |
| 5,675,844 A * | 10/1997 | Guyton | A41D 13/015 2/22 |
| 5,706,523 A * | 1/1998 | Witzel | A41D 13/1254 2/227 |
| 5,729,832 A * | 3/1998 | Grilliot | A41D 13/00 2/2.5 |
| D393,141 S * | 4/1998 | Glycenfer | D2/728 |
| 5,802,611 A * | 9/1998 | McKenzie | A41D 13/1236 2/114 |
| 5,822,802 A * | 10/1998 | Chou | A41D 13/1254 2/227 |
| 5,845,333 A * | 12/1998 | Crampton | A41D 13/065 2/24 |
| 5,887,279 A * | 3/1999 | Elting | A41D 13/1263 2/114 |
| 5,918,310 A * | 7/1999 | Farahany | A41D 13/015 2/228 |
| 5,926,851 A * | 7/1999 | Kovalik | A41D 1/06 2/114 |
| 6,079,050 A * | 6/2000 | Hooper-Jackson | A41B 9/12 2/78.1 |
| 6,115,838 A * | 9/2000 | Scholtis | A41D 1/086 2/227 |
| 6,161,222 A * | 12/2000 | Strickland | A41D 1/08 2/228 |
| 6,192,522 B1 * | 2/2001 | Schreib | A41D 1/065 2/227 |
| 6,227,937 B1 * | 5/2001 | Principe | A41B 9/12 2/407 |
| 6,233,747 B1 * | 5/2001 | Barker | A41D 27/20 2/247 |
| 6,243,878 B1 * | 6/2001 | Khemka | A41D 1/065 2/227 |
| 6,282,729 B1 * | 9/2001 | Oikawa | A41D 13/015 2/465 |
| 6,327,713 B1 * | 12/2001 | Gomez | A41D 10/00 2/227 |
| 6,421,839 B1 * | 7/2002 | Vo | A41D 13/0575 2/227 |
| 6,434,749 B1 * | 8/2002 | Grounds | A41D 13/012 2/2.15 |
| 6,477,716 B2 * | 11/2002 | Blaire | A41D 1/06 2/227 |
| 6,647,552 B1 * | 11/2003 | Hogan | A41D 13/1254 2/114 |
| 6,654,962 B2 * | 12/2003 | DeMott | A41D 13/0581 2/22 |
| 6,668,382 B1 * | 12/2003 | Wright | A61L 27/18 2/69.5 |
| 6,751,805 B1 * | 6/2004 | Austion | A41D 27/08 2/94 |
| 6,854,130 B2 * | 2/2005 | van der Sleesen | A41D 27/285 2/69 |
| 6,859,948 B2 * | 3/2005 | Melts | A41D 13/015 2/23 |
| D505,753 S * | 5/2005 | Qvortrup | D2/712 |
| 6,976,293 B2 * | 12/2005 | Traulle | A44B 19/36 24/435 |
| 7,000,261 B1 * | 2/2006 | Loffredo | A61F 5/449 2/228 |
| 7,089,598 B2 * | 8/2006 | Sallas | A41D 11/00 2/79 |
| D537,610 S * | 3/2007 | Escamillo | D2/857 |
| D553,302 S * | 10/2007 | Wiens | D29/120.1 |
| D571,078 S * | 6/2008 | Kadel | D2/712 |
| 7,389,547 B1 * | 6/2008 | Wiens | A41D 1/08 2/227 |
| 7,487,557 B2 * | 2/2009 | Bellfy | A41D 13/05 2/465 |
| 7,596,815 B2 * | 10/2009 | Grilliot | A41D 13/0007 2/227 |
| 7,752,681 B2 * | 7/2010 | Michel | A41B 9/00 2/409 |
| 7,810,172 B2 * | 10/2010 | Williams | A41D 13/1236 2/114 |
| D626,718 S * | 11/2010 | Turner | D2/712 |
| D628,769 S * | 12/2010 | Turner | D2/712 |
| D630,415 S * | 1/2011 | Nunn | D2/742 |
| D633,688 S * | 3/2011 | Turner | D2/712 |
| 7,913,319 B1 * | 3/2011 | Iannace | A41D 13/065 2/24 |
| 7,966,672 B1 * | 6/2011 | Hagerman | A41D 13/02 2/227 |
| D645,229 S * | 9/2011 | Gagnier | D2/712 |
| 8,032,951 B1 * | 10/2011 | Nestberg | A41D 13/0012 2/247 |
| 8,087,098 B2 * | 1/2012 | Kimberly | A41B 9/001 2/227 |
| D654,662 S * | 2/2012 | Lewis | D2/743 |
| D661,056 S * | 6/2012 | Cho | D2/853 |
| 8,272,073 B2 * | 9/2012 | Arensdorf | A41D 1/08 2/228 |
| 8,272,507 B1 * | 9/2012 | Crump | A45F 5/00 206/223 |
| 8,316,468 B2 * | 11/2012 | Skottheim | A41D 1/08 2/227 |
| 8,453,265 B2 * | 6/2013 | Forte | A47G 1/0616 2/115 |
| 8,453,267 B1 * | 6/2013 | Stanley | A41D 27/08 2/227 |
| 8,464,365 B1 * | 6/2013 | Nunn | A41D 1/08 2/227 |
| 8,484,765 B2 * | 7/2013 | French | A41D 27/20 2/250 |
| D703,919 S * | 5/2014 | Whaley | D2/738 |
| 8,713,715 B1 * | 5/2014 | Lewis | A41D 1/065 2/227 |
| 8,938,815 B2 * | 1/2015 | Vaughn | A41D 1/08 2/227 |
| D721,871 S * | 2/2015 | Thorn | D2/731 |
| D722,742 S * | 2/2015 | Abrams | D2/712 |
| D727,595 S * | 4/2015 | Lawson | D2/743 |
| 9,044,053 B1 * | 6/2015 | Osatchuck | A41D 13/0575 |
| 9,089,173 B2 * | 7/2015 | Krishnan | A41D 1/06 |
| D739,120 S * | 9/2015 | Young | D2/739 |
| 9,167,856 B1 * | 10/2015 | Pacific | A41D 13/065 |

(56) References Cited

U.S. PATENT DOCUMENTS

| | | | | |
|---|---|---|---|---|
| D746,544 S * | 1/2016 | Curran | | D2/738 |
| 2003/0150042 A1 * | 8/2003 | Leflet | | A41D 1/086 2/23 |
| 2003/0229930 A1 * | 12/2003 | Carlson | | A41D 13/1254 2/114 |
| 2004/0010837 A1 * | 1/2004 | Graves | | A41D 13/1245 2/114 |
| 2005/0229282 A1 * | 10/2005 | Davis | | A41D 13/0575 2/69 |
| 2006/0005292 A1 * | 1/2006 | Crye | | A41D 13/065 2/24 |
| 2006/0021115 A1 * | 2/2006 | Stanley | | A41D 13/1254 2/400 |
| 2006/0156450 A1 * | 7/2006 | McGrath | | A41D 10/00 2/114 |
| 2006/0174394 A1 * | 8/2006 | Kelly | | A41D 13/1254 2/114 |
| 2007/0044195 A1 * | 3/2007 | Atkinson | | A41B 13/00 2/24 |
| 2007/0050877 A1 * | 3/2007 | Rampersad | | A41D 13/0556 2/23 |
| 2007/0136923 A1 * | 6/2007 | Aldridge | | A41D 13/065 2/93 |
| 2007/0204376 A1 * | 9/2007 | Nunn | | A41D 1/08 2/69 |
| 2007/0245450 A1 * | 10/2007 | Feodoroff | | A41D 13/1245 2/114 |
| 2007/0271670 A1 * | 11/2007 | Hwang | | A41B 9/001 2/69 |
| 2008/0289072 A1 * | 11/2008 | Shin | | A41D 13/0556 2/23 |
| 2009/0216305 A1 * | 8/2009 | Bonner | | A41D 13/1254 607/108 |
| 2010/0235960 A1 * | 9/2010 | Johnson | | A41D 13/065 2/23 |
| 2010/0235964 A1 * | 9/2010 | Mickey | | A41D 13/129 2/228 |
| 2010/0299803 A1 * | 12/2010 | Ladra | | A41D 13/1254 2/83 |
| 2010/0313322 A1 * | 12/2010 | Sanchez | | A41D 13/065 2/24 |
| 2011/0107496 A1 * | 5/2011 | Harris | | A41D 13/1245 2/114 |
| 2011/0119814 A1 * | 5/2011 | Caliste | | A41D 13/1254 2/400 |
| 2011/0126337 A1 * | 6/2011 | Aris | | A41B 13/005 2/75 |
| 2012/0053553 A1 * | 3/2012 | Griggs | | A41B 9/00 604/396 |
| 2012/0266349 A1 * | 10/2012 | Rolando | | A41D 13/1272 2/80 |
| 2012/0284901 A1 | 11/2012 | Webb et al. | | |
| 2012/0304354 A1 * | 12/2012 | Fearon | | F41H 1/02 2/2.5 |
| 2012/0317700 A1 * | 12/2012 | Vanderburgh | | A41D 1/06 2/237 |
| 2013/0061365 A1 * | 3/2013 | Arceo | | A41D 13/065 2/24 |
| 2014/0020154 A1 * | 1/2014 | Roberts | | A41D 11/00 2/227 |
| 2014/0045397 A1 * | 2/2014 | Stachnik | | D04H 1/4291 442/67 |
| 2014/0237696 A1 * | 8/2014 | Carver | | A41D 13/0575 2/24 |
| 2014/0325734 A1 * | 11/2014 | Kuelker | | A41D 13/02 2/79 |
| 2015/0231483 A1 * | 8/2015 | Rudow | | A63B 71/1225 2/24 |
| 2016/0050988 A1 * | 2/2016 | Carver | | A41D 13/0575 2/24 |

* cited by examiner

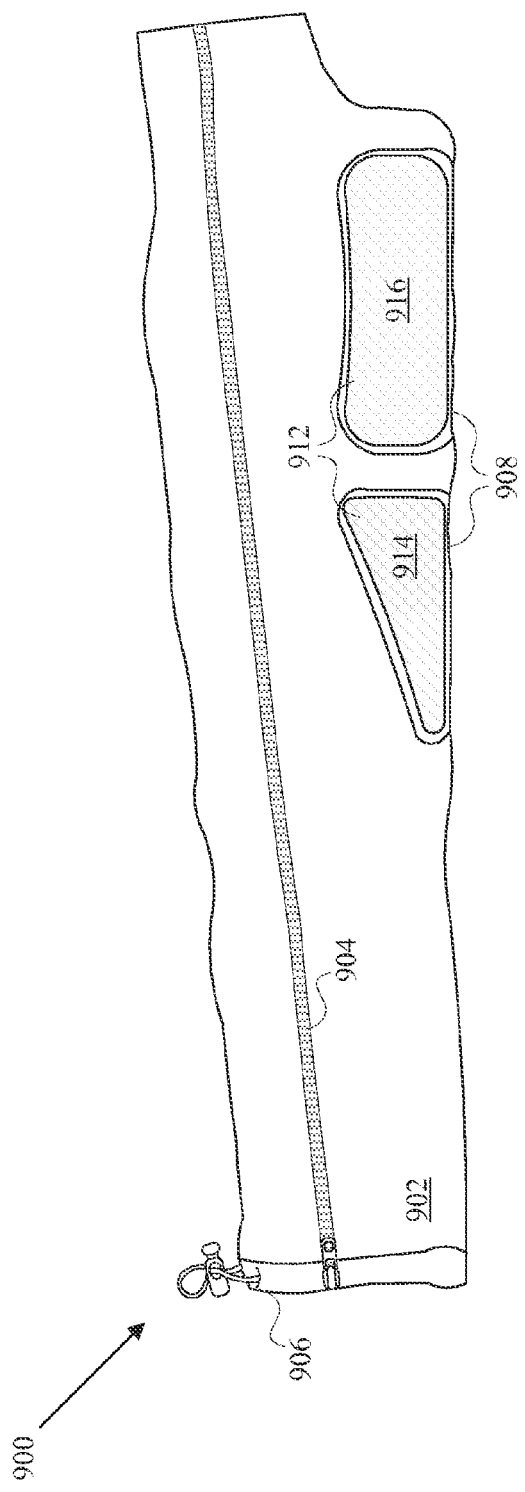

THERAPEUTIC CUSHIONING PANTS

RELATED FIELD

Some embodiments relate generally to therapeutic apparel and, in particular, to therapeutic pants that include one or more cushions.

BACKGROUND

The hips and spine are each complex parts of the human anatomy. They consist of numerous structures that can become easily misaligned through bad posture, poor sleeping position, and inactivity (e.g., sitting for too long). In addition to the vertebral skeleton, soft tissues (e.g., muscle groups) play a key role in reducing or eliminating pain. Many individuals suffer pain in these regions due to poor alignment of the spine and hips. For example, individuals may experience limited mobility or suffer weakness in one or more muscle groups during pregnancy, following surgery, due to old age, etc.

However, achieving proper alignment has been a difficult problem to solve. Traditionally, the most popular solutions have included movements designed to stretch and strengthen the muscles supporting the vertebral structure of the hips and lower back. But these movements are take substantial time and effort and, in the case of bed-ridden or elderly patients, may be difficult or impossible.

DISCLOSURE OVERVIEW

Introduced herein are various embodiments for therapeutic pants that include at least one cushion positioned to elevate, align, etc., a user's leg(s), hips, or lower back to reduce pressure, promote good posture, and improve blood circulation. Various embodiments described herein include a front panel and a rear panel made of pant material that are detachably secured along one or both lateral (i.e., outer) sides and that include at least one pocket for retaining a cushion. The therapeutic pants can include means for detachably securing the pant material that extends along one or both lateral sides of each leg, thereby allowing the therapeutic pants to be readily and repeatedly equipped and removed. In some embodiments, cinching means (e.g., elastic band, drawstring, snap fasteners) are included that allows the pant material to be secured around the user's waist, lower leg, or both.

In various embodiments, the pocket is configured to retain at least one cushion and is positioned between the user's legs (i.e., along the medial side of one or both pant legs) to align the hips. However, the pocket and cushion can also be positioned behind the user's leg to elevate the user's knee, ankle, etc. In some embodiments, a plurality of pockets are located in different areas (e.g., one pocket behind leg, one pocket between legs). The retaining pockets may also include closure means (e.g., hook-and-loop fasteners (also known as "VELCRO®"), button, zipper) that secure the cushion within the retaining pocket. The pocket can also be oriented to open in various directions (e.g., upward toward the groin, downward toward the feet, anteriorly/posteriorly away from the body).

In some embodiments, the therapeutic pants include receiving means (e.g., buttons, snap fasteners, hook-and-loop fasteners) that allow a pocket or cushion to be detachably fastened to the therapeutic pants via attaching means (e.g., button slot, snap fasteners, hook-and-loop fasteners). Together, the receiving means and the attaching means allow the pocket/cushion to be readily and repeatedly fastened and unfastened. The receiving means may also allow the user or a third party (e.g., nurse, physician, family member) to select where to fasten the pocket or cushion.

The Disclosure Overview is provided to introduce a selection of embodiments in a simplified form that are further described below in the Detailed Description. Some embodiments have other aspects, elements, features, and steps in addition to or in place of what is described above. These potential additions and replacements are described throughout the rest of the specification. Other advantages and features will become apparent when viewed in light of the Detailed Description taken in conjunction with the attached drawings and claims.

BRIEF DESCRIPTION OF THE DRAWINGS

These and other objects, features, and characteristics will become more apparent to those skilled in the art from a study of the following Detailed Description in conjunction with the appended claims and drawings, all of which form a part of this specification.

FIG. 9 is a side view of a pair of therapeutic pants according to one embodiment of the disclosure.

The figures depict various embodiments described throughout the Detailed Description for purposes of illustration only. One skilled in the art will readily recognize from the following Detailed Description that various embodiments of the structures and methods illustrated herein may be employed without departing from the principles of the invention described herein.

DETAILED DESCRIPTION

Various embodiments of therapeutic pants will now be described. The following description provides specific details for a thorough understanding and enabling description of these examples. One skilled in the art will understand, however, that embodiments may be practiced without many of these details. Additionally, some well-known structures or functions may not be shown or described in detail, so as to avoid unnecessarily obscuring the relevant description. Although the diagrams may depict components as functionally separate, such depiction is merely for illustrative purposes. It will be apparent to those skilled in the art that the components portrayed in these figures may be combined or divided into separate components.

The therapeutic pants can include at least one cushion that positions the user's leg(s), hips, or lower back in a particular alignment in order to reduce pressure, improve or promote good posture, and improve blood circulation. In some embodiments, one or more cushions are positioned between the user's legs to align the hips. In some embodiments, one or more cushions are positioned behind the user's leg (e.g., to elevate one or both knees or ankles). The therapeutic pants can include one or more retaining pockets configured to retain one or more cushions. The retaining pockets may include a closure means (e.g., hook-and-loop fasteners (also known as "VELCRO®"), button, zipper) that secures the cushion within the retaining pocket. In various embodiments, the therapeutic pants also include means for detachably securing the pant material that extends vertically along the outer sides of each leg, allowing the therapeutic pants to be easily and readily secured and removed. In some embodiments, a cinching means (e.g., elastic band, drawstring, snap fasteners) allows the pant material to be secured around the user's waist, lower leg, or both.

Figure 1:
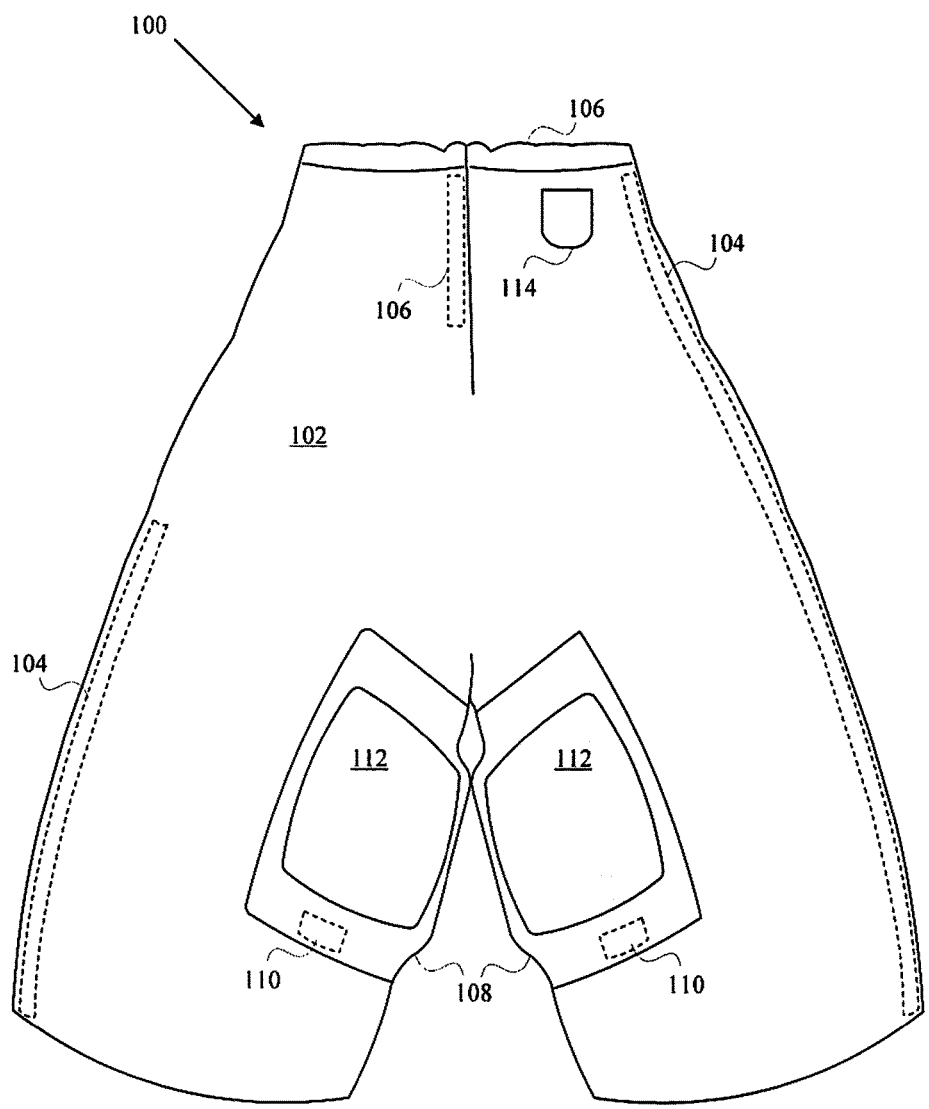
FIG. 1 is a front view of a pair of therapeutic pants according to one embodiment of the disclosure.

FIG. 1 is a front view of a pair of therapeutic pants 100 according to one embodiment of the disclosure. The therapeutic pants 100 can comprise pant material 102 that is secured along the outside of each pant leg by securing means 104. More specifically, the pant material 102 can form a front panel and a rear panel that share a common area (e.g., groin and medial side of each pant leg) and are detachably secured along the lateral side of each pant leg. The securing means 104 may be hook-and-loop fasteners (e.g., VELCRO®), buttons, snap fasteners, a zipper, ties, clips (e.g., snaphook), magnets, or any other suitable component or material. In some embodiments, a combination of the aforementioned examples are used to secure the pant material 102. As shown in FIG. 1, the securing means 104 can extend down the entirety of the therapeutic pants 100. However, in some embodiments the securing means 104 only detachably secures a portion of each pant leg. For example, the therapeutic pants 100 may only be unfastened up/down to the knee, mid-thigh, etc.

In various embodiments, the therapeutic pants 100 include cinching means 106 to cinch or secure the pant material 102 about the waist of a user. The cinching means 106 may include one or more of hook-and-loop fasteners (e.g., VELCRO®), buttons, snap fasteners, a zipper, clips, magnets, an elastic band, or a drawstring. In some embodiments, the therapeutic pants 100 can include more than one cinching means 106. For example, the therapeutic pants 100 of FIG. 1 includes VELCRO® and an elastic waistband.

The therapeutic pants 100 can also include one or more retaining pockets 108. The retaining pockets 108 can be configured to retain one or more cushions 112, which may also be referred to as pillows. The cushions 112 may be removable from the retaining pockets 108. In some embodiments, closure means 110 are used to confine one or more cushions 112 within each retaining pocket 108. The closure means 110 can include hook-and-loop fasteners (e.g., VELCRO®), buttons, snap fasteners, clips, magnets, a zipper, an elastic band, or any other suitable fastening component or material. In some embodiments, the therapeutic pants 100 include one or more pockets 114 that can be used to store personal items, medication(s), etc. The pockets 114 can be located along the side of the pant leg, on the rear panel (i.e., behind the user's leg), or on the front panel (i.e., in front of the user's leg as shown in FIG. 1).

Figure 2:
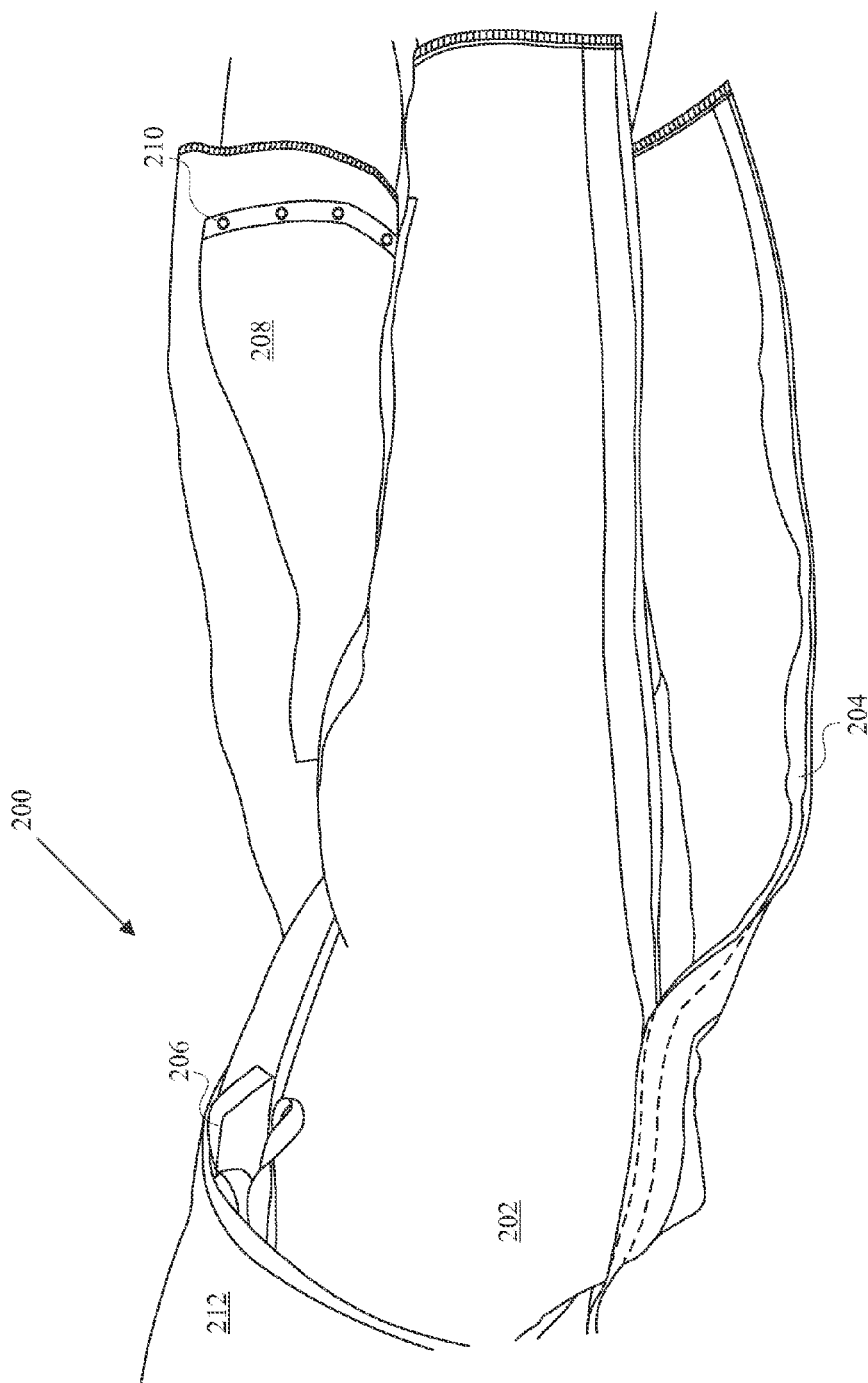
FIG. 2 is a side view of a pair of therapeutic pants according to one embodiment of the disclosure.

FIG. 2 is a side view of a pair of therapeutic pants 200 according to one embodiment of the disclosure. The therapeutic pants 200 can include washable pant material 202 that is secured along the outside of each pant leg by securing means (e.g., VELCRO®) 204, a buttonless fly opening and drawstring 206 for securing the pant material 202 about the waist of a user 212, one or more retaining pockets 208 positioned along the inside of each pant leg, and closure means (e.g., snap fasteners) 210 for securing one or more cushions within each retaining pocket 208. In various embodiments, the therapeutic pants 200 are detachably secured along the entirety or a portion of the pant leg. Detachably secured means that the therapeutic pants 200 are capable of being readily and repeatedly equipped and removed. While FIG. 2 illustrates the therapeutic pants 200 as being secured by hook-and-loop fasteners (e.g. VELCRO®) 204, one skilled in the art will recognize that many other fastening materials and components can be employed, including those described above with respect to FIG. 1.

In some embodiments, the pant material 202 is reusable. For example, the pant material 202 may be a washable organic fabric. The pant material 202 may be non-allergenic, antimicrobial, fire-retardant, etc. In some embodiments, the pant material 202 is designed to be disposable (e.g., single-use). For example, the pant material 202 may be nonwoven polyethylene designed for hospital use that has high impact strength, low water absorption, is recyclable, etc. One skilled in the art will appreciate the pant material and cushions may be reusable or disposable depending on the desired application. For example, the pant material 202 may be washable and reusable, while the cushions may be disposable, and vice versa.

Figure 3:
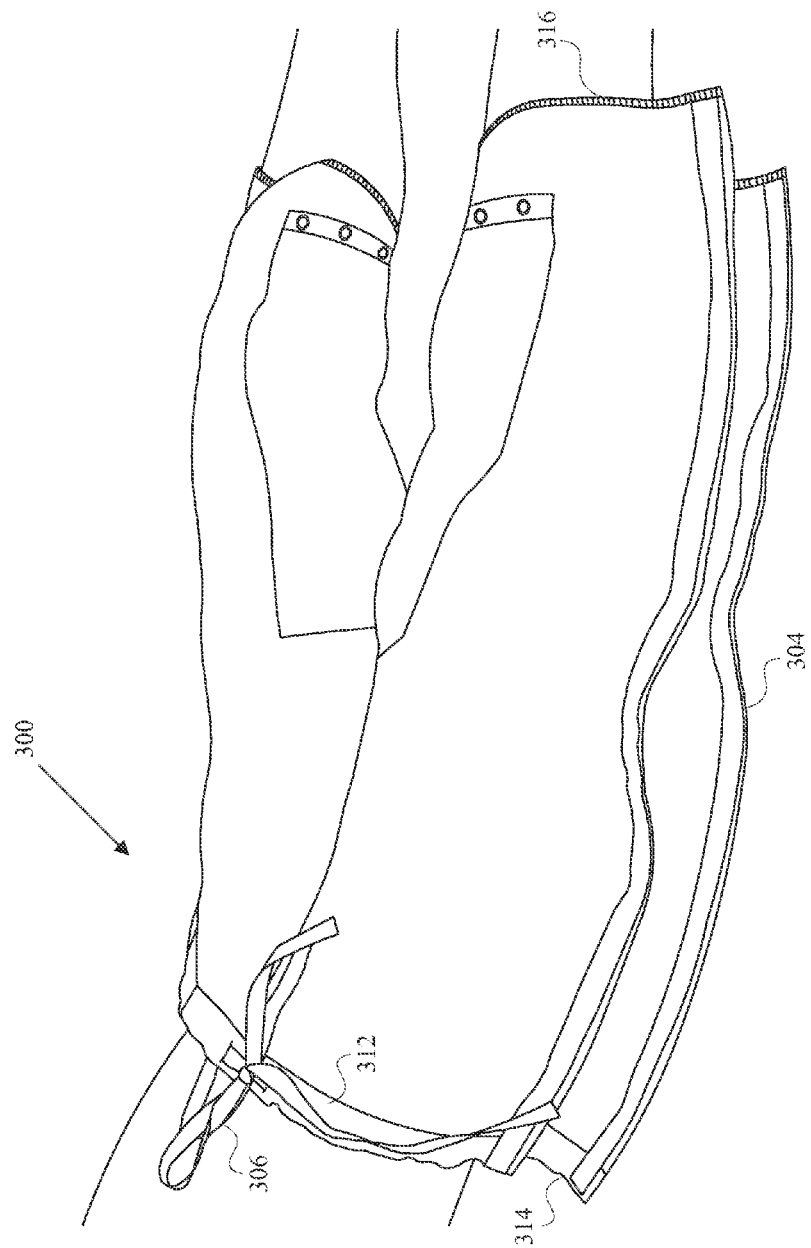
FIG. 3 is a side view of a pair of therapeutic pants according to one embodiment of the disclosure.

FIG. 3 is a side view of a pair of therapeutic pants 300 according to one embodiment of the disclosure. The therapeutic pants 300 may be, for example, the therapeutic pants 200 of FIG. 2. FIG. 3 illustrates the hook-and-loop fasteners (e.g. VELCRO®) 304 as being completely unsecured. In some embodiments, the therapeutic pants 300 include an elastic front waistband 312 that extends along at least a portion of the front panel of the therapeutic pants 300. The therapeutic pants 300 may also include an elastic rear waistband 314 that extends along at least a portion of the rear panel of the therapeutic pants 300. In various embodiments, the front panel and rear panel share a common groin area and can be detachably secured by the hook-and-loop fasteners (e.g., VELCRO®) 304, or similar fastening material or component, that extends down the lateral (e.g., outer) side of each pant leg. In some embodiments, the elastic band extends around the entirety of the user's waist. For example, a single continuous elastic band may be used if the hook-and-loop fasteners (e.g., VELCRO®) 304 only secures a lower portion (e.g., below the user's knee) of each pant leg.

The therapeutic pants 300 can also include an elastic band 316, drawstring and drawstring lock, tie, etc. that extends around a portion of the bottom of one or both pant legs. In some embodiments, the elastic band 316 extends around the entirety of the pant leg. For example, a continuous elastic band 316 may be used if the hook-and-loop fasteners (e.g., VELCRO®) 304 only secures an upper portion (e.g., above the user's knee) of each pant leg. One skilled in the art will recognize that the hook-and-loop fasteners (e.g., VELCRO®) 304, or alternative securing means, can cover the entirety or a portion of each pant leg and that the portion may be located anywhere along the pant leg. In some embodiments (e.g., therapeutic pants 100 of FIG. 1), the bottom of the pants may be open (e.g., loose).

Figure 4:
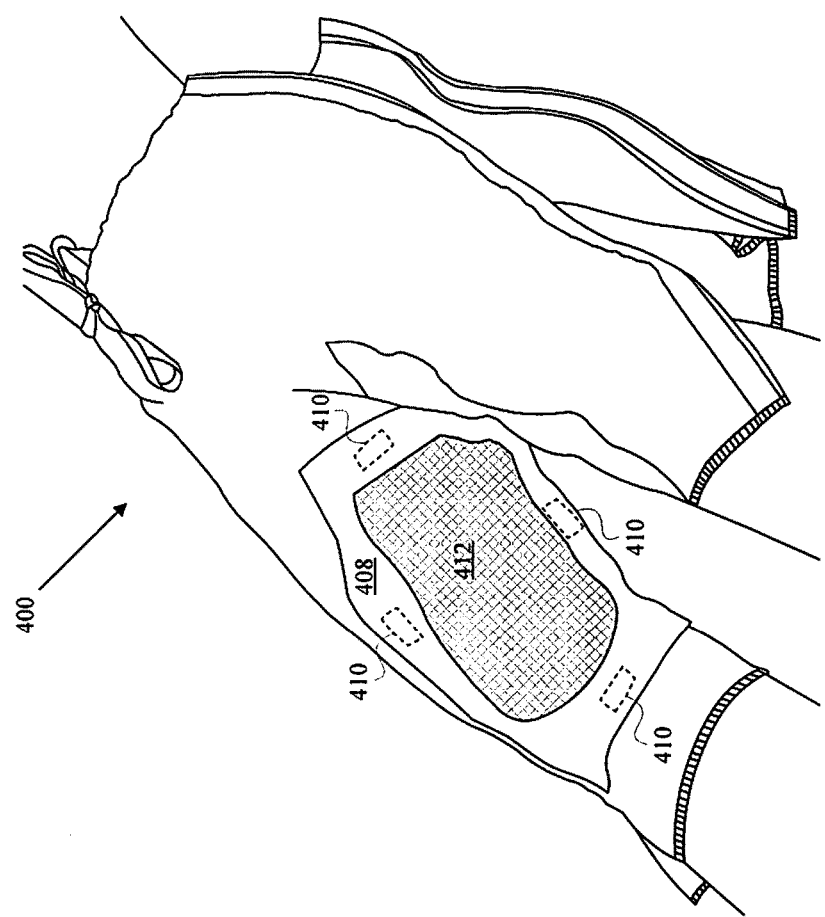
FIG. 4 is a perspective view of a pair of therapeutic pants according to one embodiment of the disclosure.

FIG. 4 is a perspective view of a pair of therapeutic pants 400 according to one embodiment of the disclosure. The therapeutic pants 400 can include a retaining pocket 408, closure means 410 for the retaining pocket 408, and a cushion 412. Although closure means 410 is illustrated as hook-and-loop fasteners (e.g., VELCRO®) in FIG. 4, the closure means 410 can include buttons, snap fasteners, clips, magnets, a zipper, an elastic band, etc. In various embodiments, the retaining pocket 408 can be positioned in different orientations. For example, the retaining pocket 408 can be oriented to open downward (e.g., toward the user's foot). As another example, the retaining pocket 408 can be positioned to open upward (e.g., towards the user's groin/waist). Further yet, the retaining pocket 408 can be positioned to open laterally (e.g., anteriorly or posteriorly away from the user's body). In some embodiments, such as those where the retaining pocket 408 opens upward or laterally, closure means 410 may be unnecessary and not present.

Figure 5:
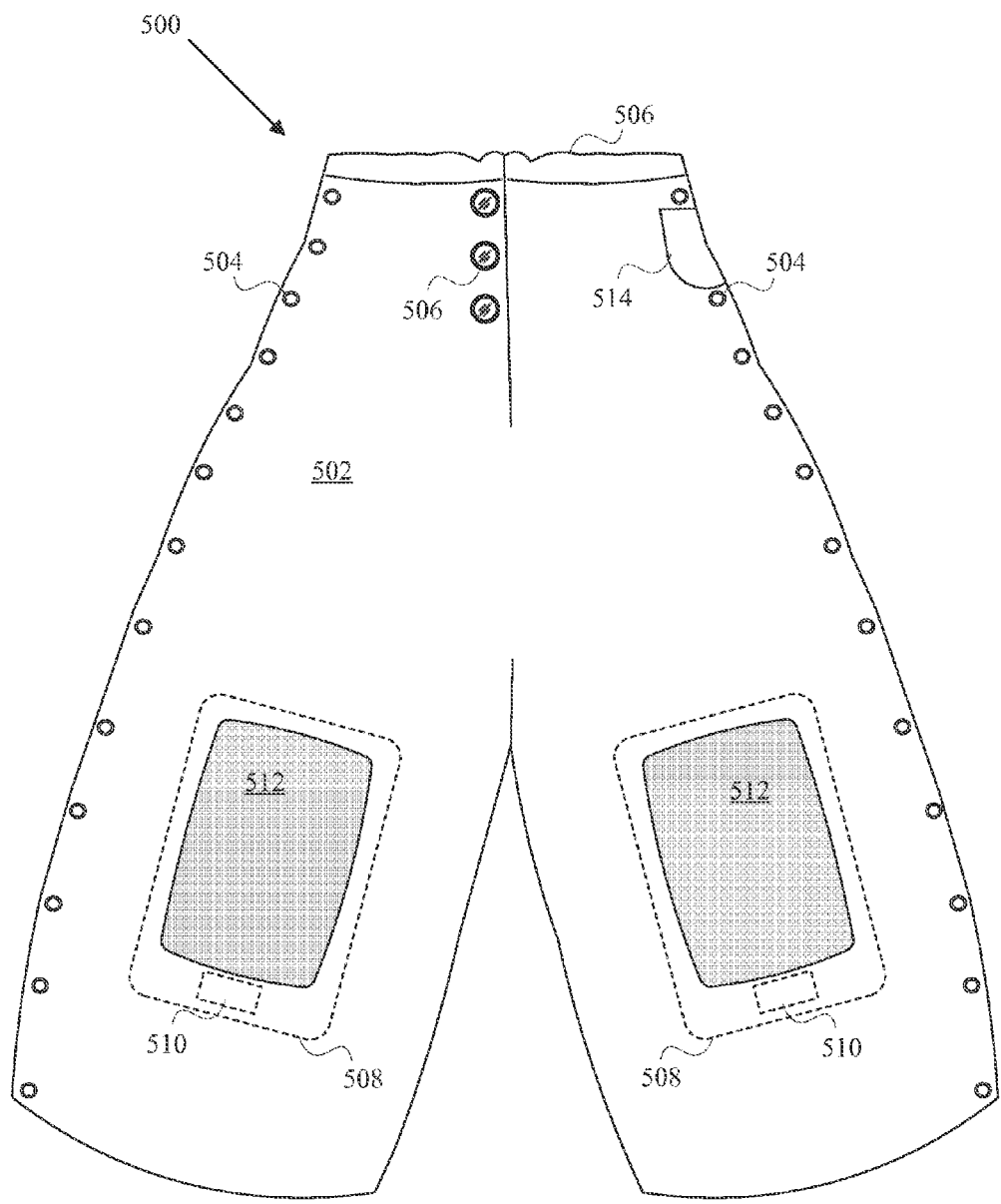
FIG. 5 is a front view of a pair of therapeutic pants according to one embodiment of the disclosure.

FIG. 5 is a front view of a pair of therapeutic pants 500 according to one embodiment of the disclosure. The therapeutic pants 500 can comprise pant material 502 that is secured along the lateral sides of each pant leg by securing means 504. The securing means 504 is illustrated in FIG. 5 as a set of snap fasteners positioned along the outside of each pant leg. However, the securing means 504 can also include hook-and-loop fasteners (e.g., VELCRO®), buttons, a zipper, ties, clips, magnets, or any other suitable fastening material or component. In some embodiments, the securing means 504 may not be spaced uniformly. In some embodiments, fastening components such as snap fasteners, buttons, etc., could be spaced more closely together in certain areas (e.g., upper thigh) where the user or a third party (e.g., nurse, physician) is unlikely to need access. A higher density of fastening components ensure the therapeutic pants 500 are substantially more secure.

In some embodiments, the therapeutic pants 500 include cinching means 506 to cinch (i.e., secure) the pant material 502 about the waist of a user. As described above, the cinching means 506 may include hook-and-loop fasteners (e.g., VELCRO®), buttons, snap fasteners, a zipper, clips, magnets, an elastic band, a drawstring, etc. For example, the therapeutic pants 500 of FIG. 5 includes a set of snap fasteners and an elastic waistband.

The therapeutic pants 500 can also include one or more retaining pockets 508 that are configured to retain one or more cushions 512. The cushions 512 may be integrated into or removable from the retaining pockets 508. In some embodiments, the retaining pockets 508 include closure means 510 for confining the one or more cushions 512. As described above, the closure means 510 can include hook-and-loop fasteners (e.g., VELCRO®), buttons, snap fasteners, clips, magnets, a zipper, an elastic band, etc. In some embodiments, the therapeutic pants 500 include one or more pockets 514 that can be used to store personal items, medication(s), etc.

The retaining pockets 508 can be positioned in various locations along the front, back, lateral side(s) and/or medial side(s) of the pant leg(s). For example, FIG. 1 illustrates the retaining pockets 108 as positioned along the inside of the user's legs (i.e., medial sides of each pant leg). As another example, FIG. 5 illustrates the retaining pockets 508 as positioned behind the user's legs (i.e., posterior side of each pant leg). One skilled in the art will recognize that some embodiments may include a combination of these examples (e.g., one or more retaining pockets behind the leg and one or more retaining pockets along the inside of the leg). In some embodiments, the retaining pockets 508 are arranged to elevate or align a particular body part, thereby improving circulation, comfort, posture, etc. For example, the retaining pockets 508 may be positioned behind the user's hamstring to elevate the knee, behind the user's calf to elevate the ankle, etc.

Figure 6:
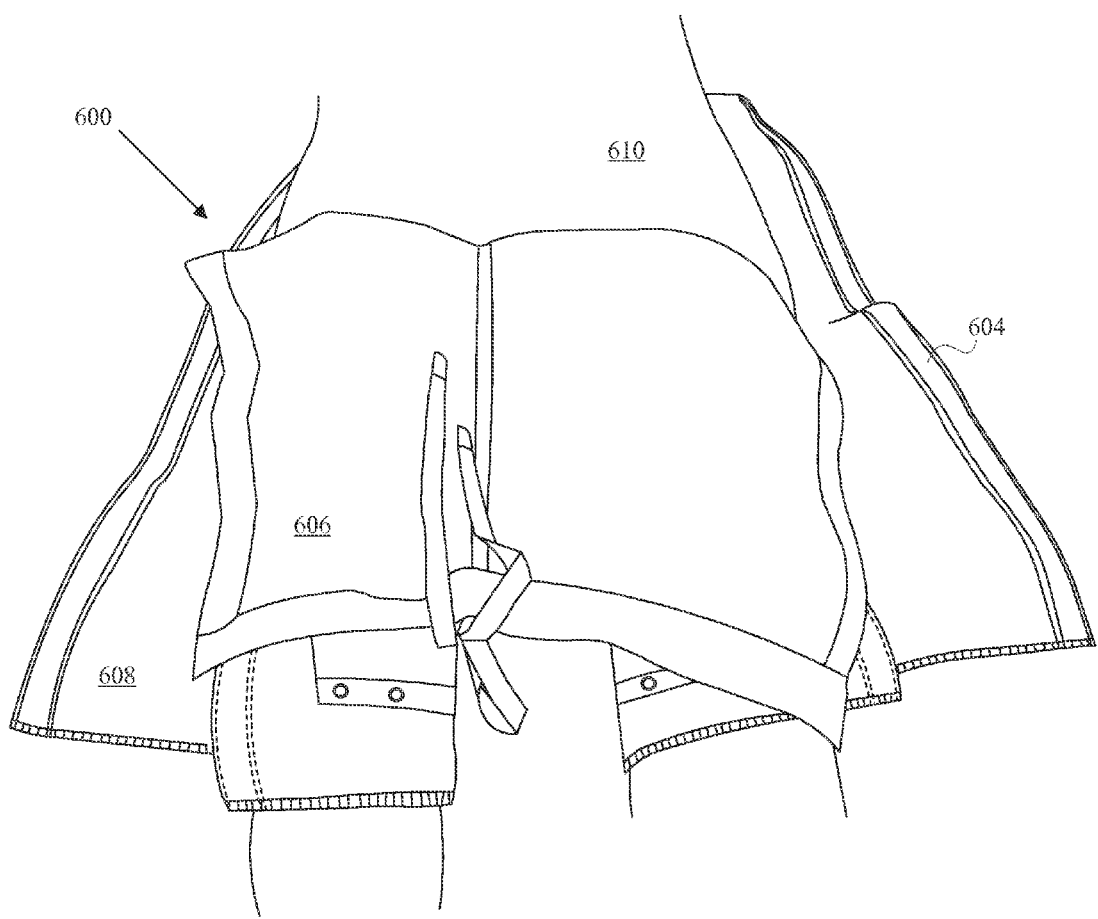
FIG. 6 is a front view of a pair of therapeutic pants worn by a user according to one embodiment of the disclosure.

FIG. 6 is a front view of a pair of therapeutic pants 600 worn by a user 610 according to one embodiment of the disclosure. The therapeutic pants 600 can be removed and/or altered when securing means 604 is placed along a portion of each pant leg (e.g., from waist to knee). The securing means 604 may be placed along a portion of each pant leg if the user or a third party (e.g., nurse, physician) are likely to need access to a particular area of the user's body (e.g., upper thigh or groin area). The therapeutic pants 600 can be removed and/or altered when the securing means 604 are unfastened. For example, FIG. 6 illustrates therapeutic pants 600 that include a front panel 606 and a rear panel 608, which share a common groin area and can be fastened together by the securing means 604 that extend down the outside of each pant leg (e.g., left and right lateral sides). When the securing means 604 are unfastened, the front panel 606 can be folded away from the user's waist, which may allow a third party (e.g., nurse, physician) to access the user's upper thigh or groin area. Similarly, the front panel 606 could be folded away from the user's shins, knees, etc. One skilled in the art will recognize the rear panel 608 could similarly be folded away.

Figure 7:
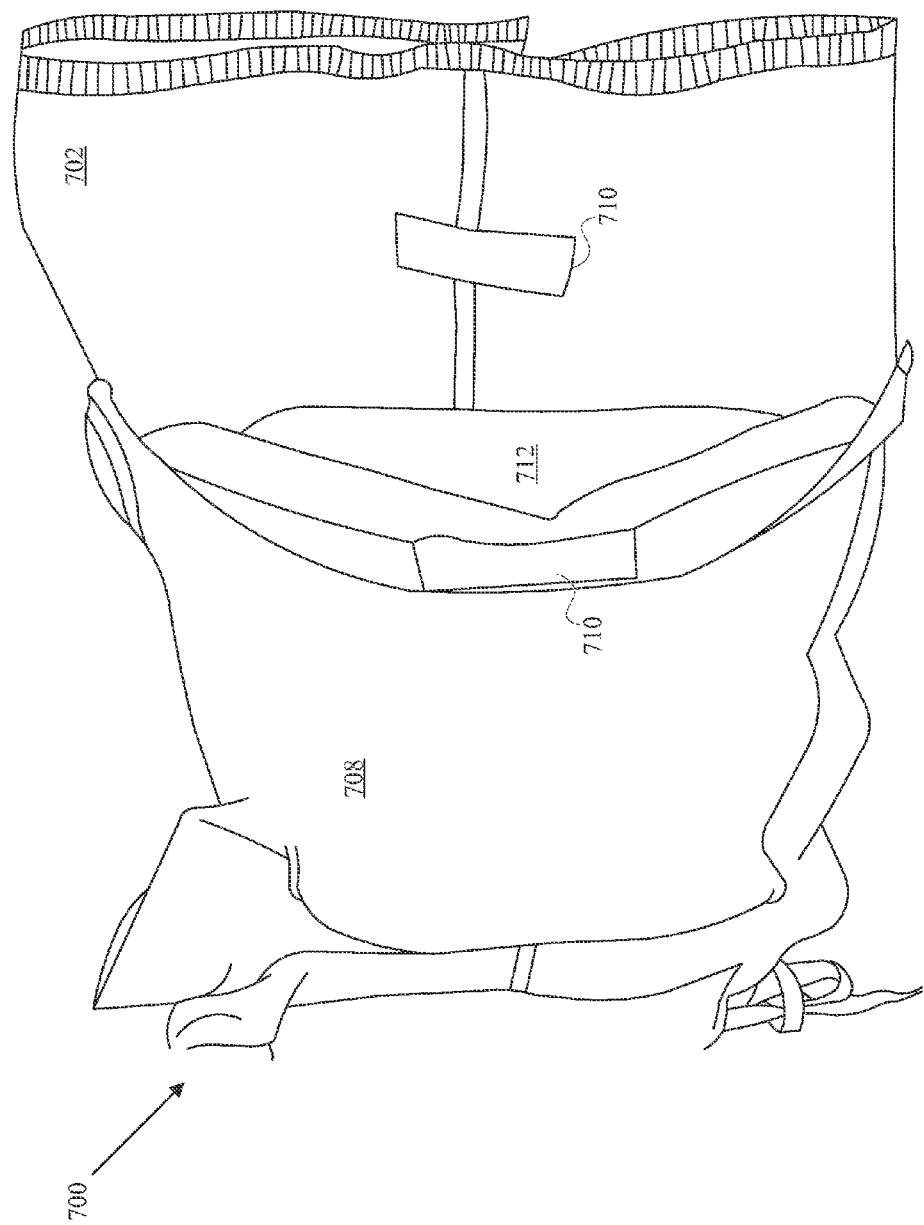
FIG. 7 is a side view of a retaining pocket including a cushion according to one embodiment of the disclosure.

FIG. 7 is a side view of a retaining pocket 708 including a cushion 712 according to one embodiment of the disclosure. The retaining pocket 708 can be closed via closure means 710, which is illustrated as adhesive strips of hook-and-loop fasteners (e.g., VELCRO®) in FIG. 7. In various embodiments, the retaining pockets 708 are permanently or semi-permanently affixed to the pant material 702. For example, the retaining pocket 708 may be sewn to the pant material 702. In some embodiments, the retaining pockets 708 are detachably engageable with the pant material 702, as will be discussed below with respect to FIGS. 10A-C. More specifically, the retaining pockets 708 may be readily attached to and detached from the pant material 702 in some embodiments, thereby allowing the location of the retaining pockets 708 to change.

The retaining pockets 708 may also be fitted for cushions 712 of a particular size. For example, therapeutic pants 700 designed for adults may have larger retaining pockets 708 for larger cushions 712 than those therapeutic pants 700 designed for children. The cushions 712 can also come in a variety of shapes, sizes, firmness level, materials, etc. Generally, the width and length of the cushion 712 vary from 6 inches to 19 inches, while the height varies from 0.5 inches to 3 inches. For example, if two retaining pockets 708 are positioned along the inside of the user's legs (medial sides of each pant leg as illustrated in FIG. 1), each cushion 712 may be approximately 1 inch in height, thereby improving alignment of the user's hips by a total of approximately 2 inches. One skilled in the art will recognize that while general ranges have been provided for the width, length, and height of the cushions, values outside of those ranges are possible and, in certain instances, may be desirable.

The cushions 712 may be constructed of memory foam, latex, feathers, polyester, silicone or Polyurethane gel, Polystyrene beads, cotton, air pockets, natural filling, etc. A natural filling may be, for example, lavender, flax seeds, buckwheat, wool, millet, kapok, etc. A plurality of cushions 712 made of different materials (e.g., one polyester cushion, one memory foam cushion) may be used in some embodiments. In some embodiments, a cushion is made of (e.g., filled with) more than one of the aforementioned materials. Different cushion materials can be selected on the basis of firmness, sensitivity to allergens, desired properties (e.g., antimicrobial, flame-retardant), etc. The cushions 712 can also include a casing or cover that is reusable (e.g., washable nonwoven fabric) or disposable. The pant material 702, retaining pockets 708, cushion 712, and/or cushion cover can be made of woven or non-woven fabric designed for particular users or situations (e.g., hospital use, physical therapy, pregnancy). Washable pant material 702 can be used with washable or disposable cushions 712.

While the cushions 712 need not be a particular shape, one skilled in the art will recognize that particular shapes may provide appreciable benefits, as will be discussed below with respect to FIG. 9. In some embodiments, the retaining pockets 708 include a cushioning layer within the opening of each retaining pocket 708. One or more cushioning layers may be integrated into or attached to (e.g., sewn) the pant material to provide support without the use of cushions 712. In various embodiments, the retaining pockets 708 are also designed to hold hot and/or cold packs. For example, a pair of therapeutic pants 700 may include a retaining pocket 708 positioned behind the user's knee, which allows the user to elevate the knee, and another retaining pocket 708 in front of the knee, which allows the user to apply a hot/cold pack.

Figure 8:
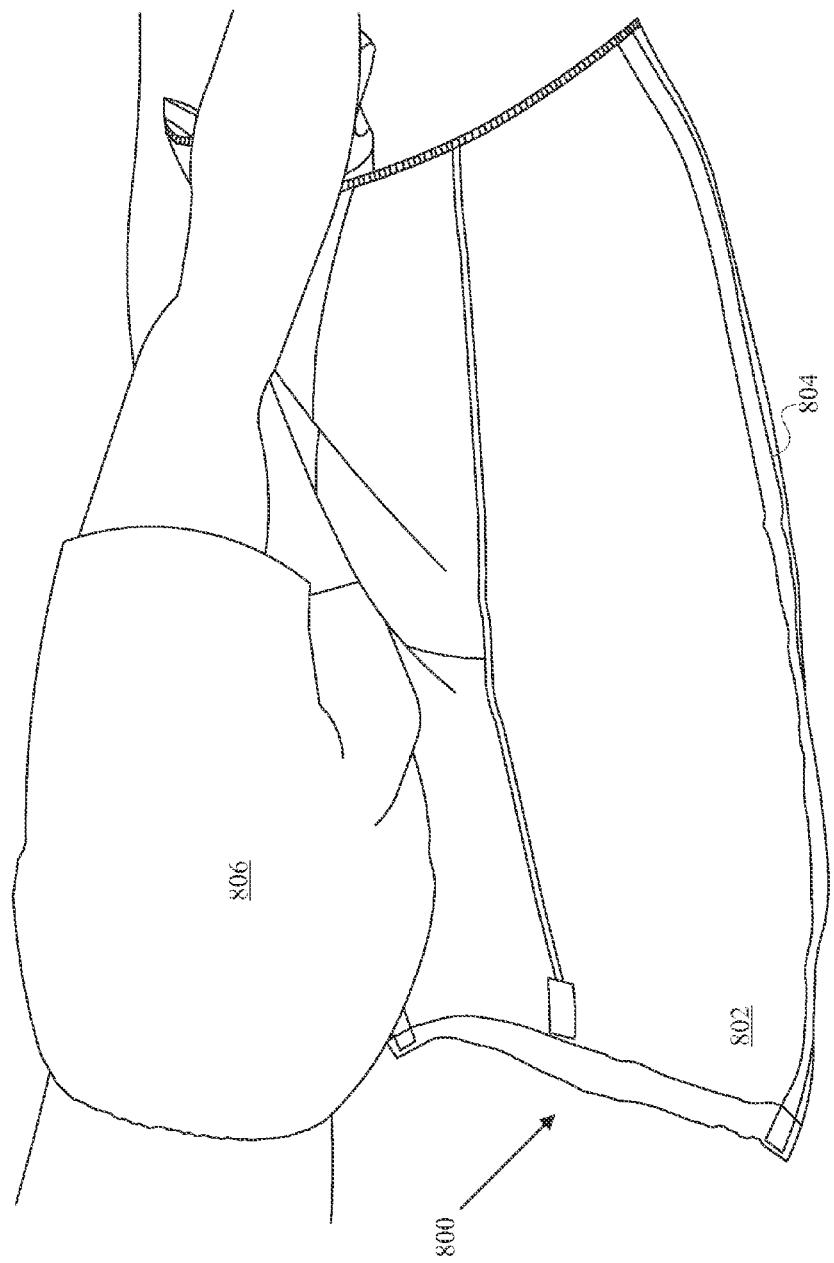
FIG. 8 is a perspective view of a pair of therapeutic pants worn by a user according to one embodiment of the disclosure.

FIG. 8 is a perspective view of a pair of therapeutic pants 800 worn by a user 806 according to one embodiment of the disclosure. The therapeutic pants 800 can include pant material 802 that is detachably secured by securing means 804 that extend down the outside (e.g., left lateral side and right lateral side) of each pant leg. When the securing means 804 are unsecured (e.g., unfastened, unbuttoned, untied), the user 806 or a third party (e.g., nurse, caretaker, family member) can remove the therapeutic pants 800. The securing means 804 allow the user or the third party to readily and repeatedly equip and remove the therapeutic pants 800.

Although various embodiments make reference to therapeutic pants, the implementation details described herein could also be applied to shorts, three-quarter pants, etc. Similarly, various implementation details should be applied to other articles of clothing, such as shirts, headwear, arm/leg sleeves, etc.

FIG. 9 is a side view of a pair of therapeutic pants 900 according to one embodiment of the disclosure. The therapeutic pants 900 can include pant material 902 that is secured along the outside of each pant leg by securing means 904 (illustrated as a zipper), cinching means 906 (illustrated as a drawstring and drawstring lock), and one or more retaining pockets 908 configured to retain one or more cushions 912. As shown in FIG. 9, the cushions 912 can be different dimensions and can be positioned at various positions along the back, front, and/or inside of the user's leg. Moreover, as shown in FIG. 9, the therapeutic pants 900 may taper to a narrower bottom near the hem line (e.g., rather than flare out near the hem line).

Generally, the cushions 912 need not be a particular shape. However, one skilled in the art will recognize that certain shapes may provide appreciable benefits for patients suffering from a particular injury, patients needing specific alignment(s), etc. For example, the therapeutic pants 900 illustrated in FIG. 9 include two cushions 912, a first wedge-like cushion 914 that is positioned behind the user's hamstring, and a second cuboid cushion 916 that is positioned behind the user's calf. Together, the first cushion 914 and second cushion 916 can elevate the user's lower leg. Many other shapes may be used to serve similar purposes, such as a polyhedron having one or more sloped sides, a prism, a cylinder, etc. In some embodiments, the therapeutic pants 900 include a plurality of retaining pockets 908, each configured to retain one cushion 912. In some embodiments, the therapeutic pants 900 include a single retaining pocket 908 configured to retain a plurality of cushions 912 (e.g., both first cushion 914 and second cushion 916).

Figure 10A:
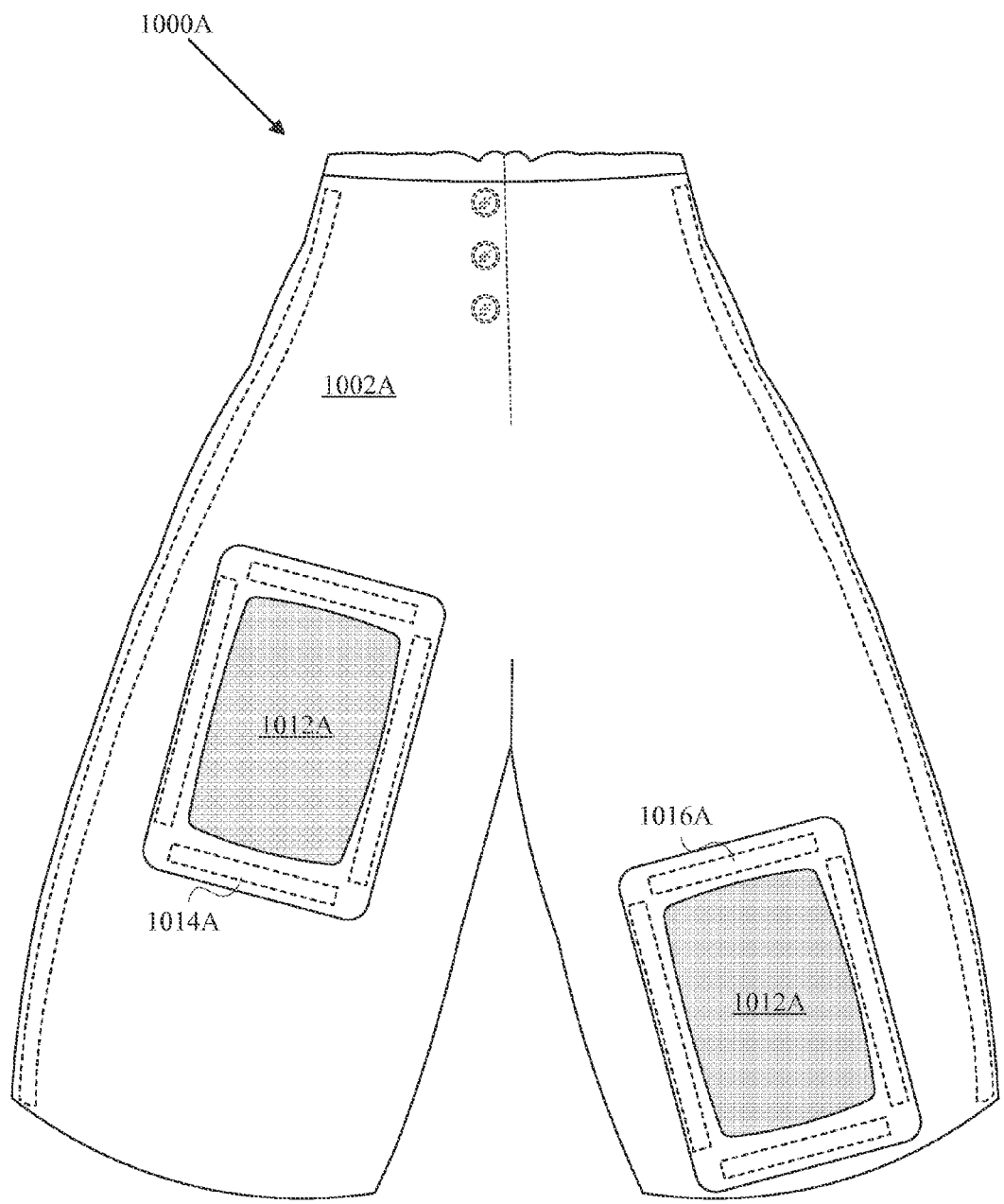
FIGS. 10A-C are rear views of various pairs of therapeutic pants and detachable engageable cushions according to embodiments of the disclosure.
Figure 10B:
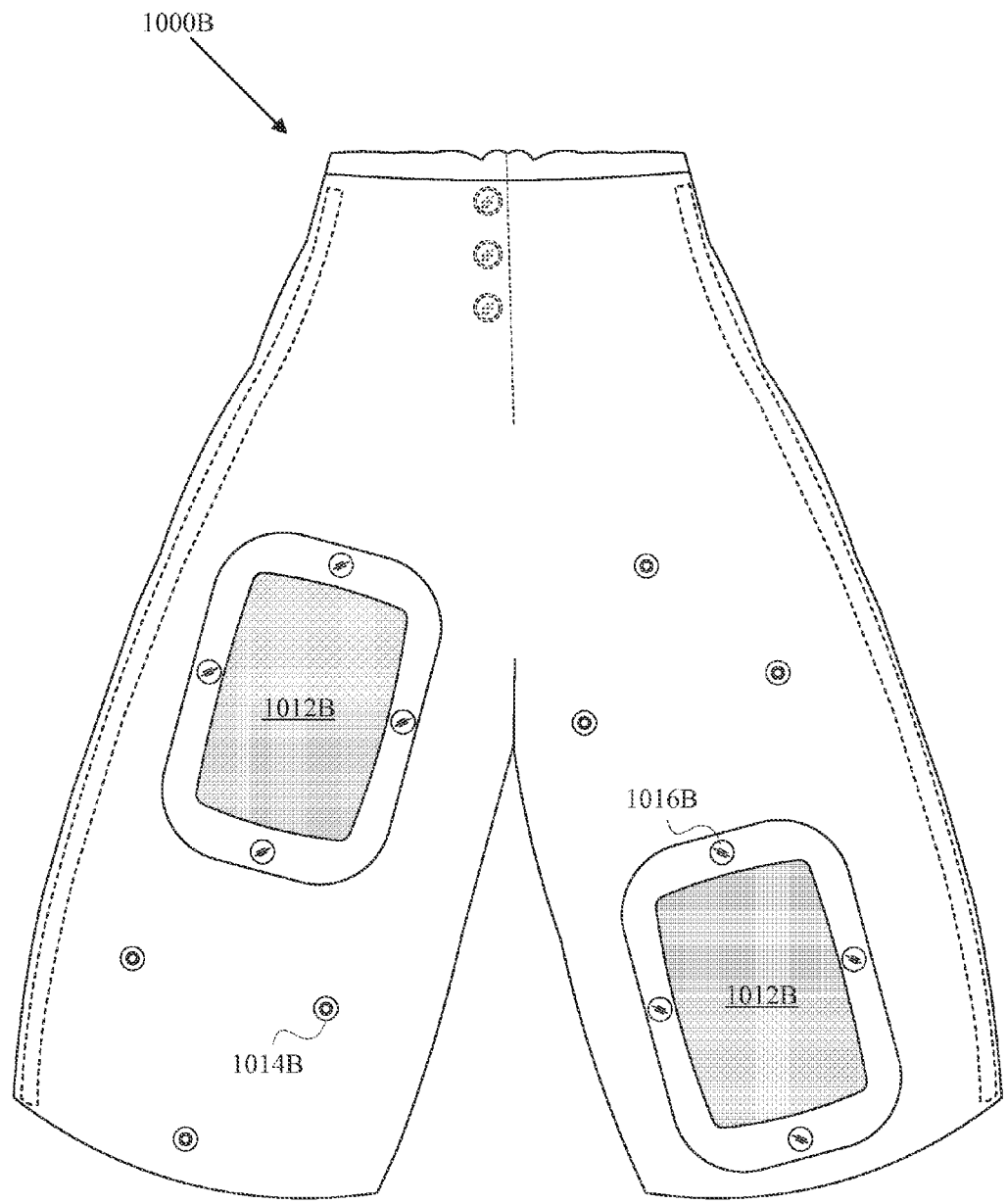
Figure 10C:
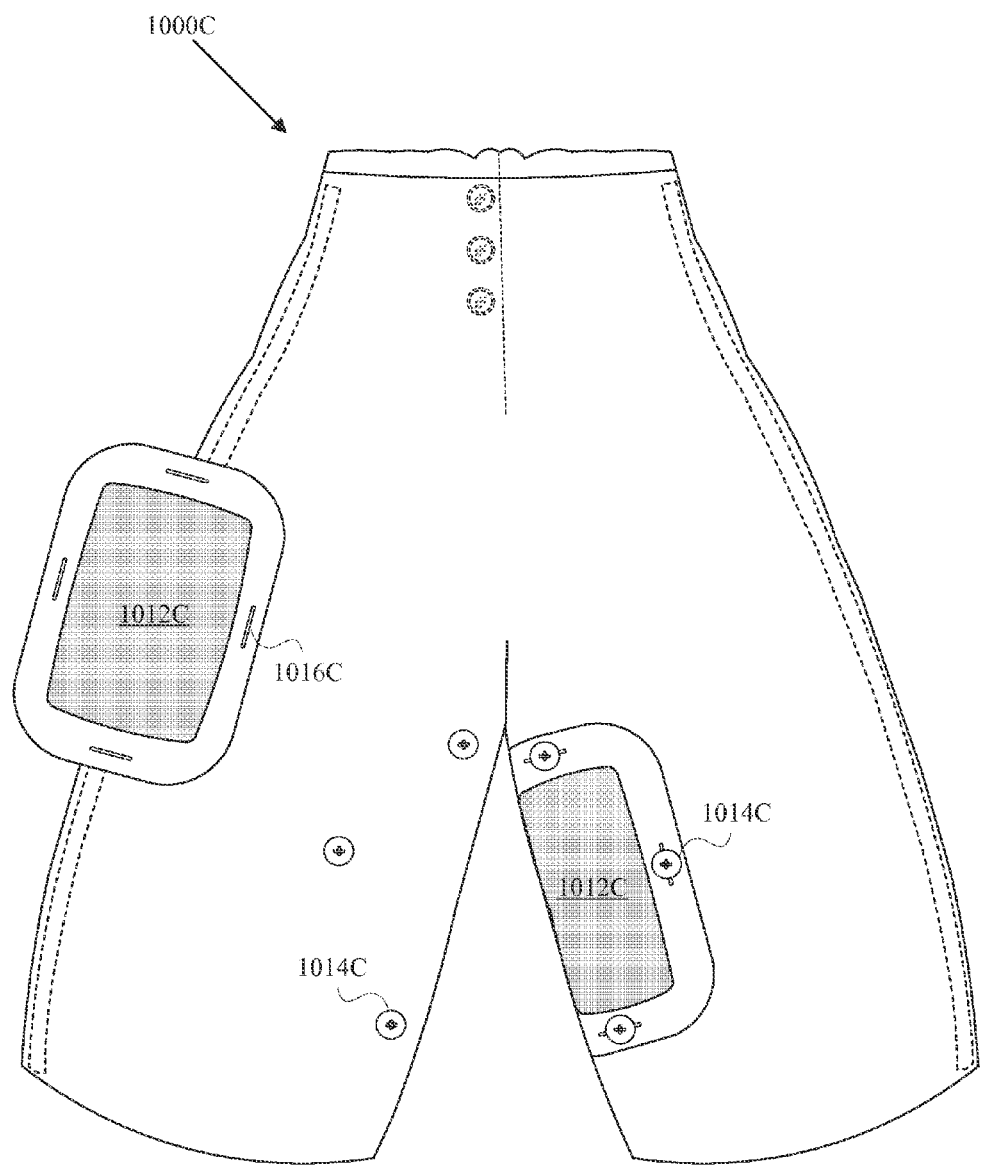

FIGS. 10A-C are rear views of various pairs of therapeutic pants 1000A-C and detachable engageable cushions 1012A-C according to embodiments of the disclosure. In some embodiments, the therapeutic pants 1000A-C include receiving means 1014A-C that are detachably engageable with attaching means 1016A-C of a cushion 1012A-C. The receiving means 1014A-C and attaching means 1016A-C, together, permit the cushion 1012A-C to be easily and readily attached to and removed from the therapeutic pants 1000A-C. The receiving means 1014A-C and attaching means 1016A-C will, in general, be complementary in nature, which allows the attaching means 1016A-C to be fixed directly to the receiving means 1014A-C without the use of any tools (e.g., sewing machine). For example, the receiving means 1014A-C and attaching means 1016A-C may include hook-and-loop fasteners (e.g., VELCRO®), tie-able strings, a button and button receiving slot, compatible snap fasteners, a zipper, buckle, a clip and clip receiver, attracting magnets, etc.

In some embodiments, the pant material 1002A itself serves as the receiving means 1014A. For example, if the attaching means 1016A includes one or more strips of hook-and-loop fasteners (e.g., VELCRO®) (as illustrated in FIG. 10A), a particular pant material 1002A (e.g., nylon, polyester) may be selected that allows the VELCRO® to engage the pant material 1002A, which causes the cushion(s) 1012A to become fastened to the therapeutic pants 1000A. In such embodiments, the user can wear the therapeutic pants 1000A and selectively attach and remove the detachably engageable cushions 1012A when desired or necessary.

In some embodiments, the receiving means 1014B, the attaching means 1016B, or both are moveable. Consequently, the position and alignment of the cushion(s) 1012B may be modified by the user or a third party (e.g., nurse, family member). For example, the therapeutic pants 1000B may include a plurality of snap fasteners in various locations (as illustrated in FIG. 10B) that allow the cushion 1012B to be attached in different positions and orientations.

As yet another example, the receiving means 1014C can be located (e.g., fixed) in one or more particular locations. For example, the therapeutic pants 1000C may include a set of buttons 1014C positioned along the inside of each pant leg (as shown in FIG. 10C) that permit attachment of the cushion 1012C via button receiving slots 1016C.

Figure 11:
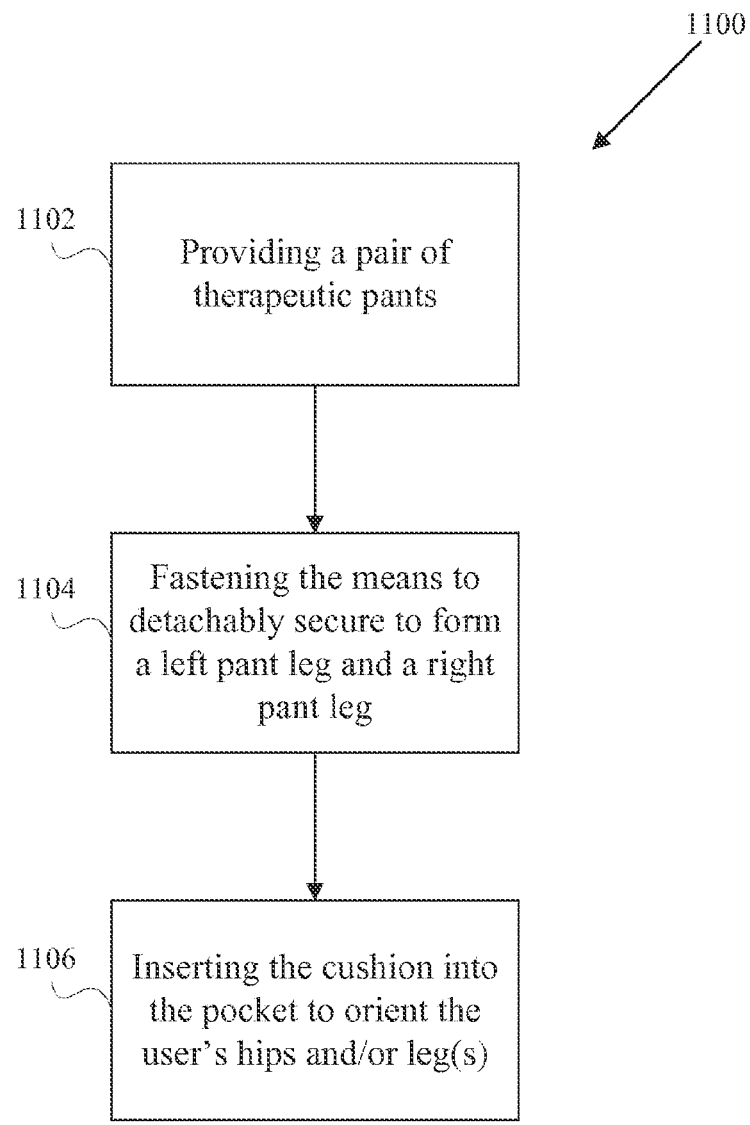
FIG. 11 is a process for improving the alignment and positioning of a user's hips, leg(s), etc., according to various embodiments of the disclosure.

FIG. 11 is a process 1100 for improving the alignment and positioning of a user's hips, leg(s), etc. At block 1102, a pair of therapeutic pants are provided. The therapeutic pants can be any of those embodiments described above (e.g., therapeutic pants 100 of FIG. 1, therapeutic pants 500 of FIG. 5). The therapeutic pants can include a pocket and means to detachably secure the pant material along the entirety or part of the left lateral side, the right lateral side, or both. At block 1104, the means to detachably secure are fastened to form a left pant leg and a right pant leg. At block 1106, a cushion is inserted into the pocket to orient the user's hips, leg(s), ankle, etc. in a particular alignment or direction. For example, the pocket and cushion can be located between the pant legs to align the user's hips, as shown in FIG. 1. As another example, the pocket and cushion can be located on a rear panel of the therapeutic pants to elevate the user's leg, as shown in FIG. 5.

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen in order to best describe the principles of the invention and its practical applications, thereby enabling others skilled in the relevant art to understand the claimed subject matter, the various possible embodiments, and the various modifications that are suited to particular uses contemplated herein.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted using capitalization, italics or quotation marks. The use of highlighting has no influence on the scope and meaning of a term; the scope and meaning of a term is the same, in the same context, whether or not it is highlighted. It will be appreciated that the same element can be described in more than one way.

Consequently, alternative language and synonyms may be used for any one or more of the terms discussed herein. Special significance should not be placed upon whether or not a term is elaborated or discussed herein. Synonyms for certain terms are provided (e.g., cushion, pillow). A recital of one or more synonyms does not exclude the use of other synonyms. The use of examples anywhere in this specification, including examples of any terms discussed herein, is meant to be illustrative only and is not intended to further limit the scope or meaning of the disclosure or of any exemplified term. Likewise, the disclosure is not limited to the various embodiments given in the Detailed Description.

Reference in this specification to "one embodiment" or "an embodiment" means that a particular feature, structure, or characteristic described in connection with the embodiment is included in at least one embodiment of the disclosure. The appearances of the phrase "in one embodiment" in various places throughout the specification are not necessarily all referring to the same embodiment, nor are separate or alternative embodiments mutually exclusive of other embodiments. Moreover, various features are described that may be exhibited by some embodiments but not by others. Similarly, various features are described that may be requirements for some embodiments but not others.

While the Detailed Description describes certain embodiments and the best mode contemplated, no matter how detailed the above appears in text, the invention can be practiced in many ways. The embodiments may vary considerably in their implementation details, while still being encompassed by the specification. As noted above, the particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed herein, unless the terms have been explicitly defined in the Detailed Description. Accordingly, the actual scope of the invention encompasses not only the disclosed embodiments, but also all equivalent ways of practicing or implementing the embodiments under the claims.

Unless the context clearly requires otherwise, throughout the Detailed Description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements. Additionally, the words "herein," "above," "below," and words of similar import shall refer to the specification as a whole and not to any particular portion(s) of this specification. Where the context permits, words in the singular or plural form may also include the plural or singular form respectively. The word "or," in reference to a list of two or more items, covers all of the following interpretations of the word: any of the items in the list, all of the items in the list, and any combination of the items in the list.

The language used in the specification has been principally selected for readability and instructional purposes, and it may not have been selected to delineate or circumscribe the inventive subject matter. Therefore, it is intended that the scope of the invention be limited not by this Detailed Description, but rather by any claims that issue on an application based hereon. Accordingly, the disclosure of various embodiments is intended to be illustrative, but not limiting, of the scope of the invention, which is set forth in the following claims.

What is claimed is:

1. A pair of therapeutic pants to be worn by a user, the pair of therapeutic pants comprising:
   a front fabric panel and a rear fabric panel that share a common groin area,
      wherein the front and rear fabric panels are comprised of nonwoven polyethylene,
      wherein each of the front and rear fabric panels includes a top edge, a left outer edge, and a right outer edge, and
      wherein adhesive strips of hook-and-loop fasteners are disposed along a portion of the left outer edges and the right outer edges of the front and rear fabric panels, the portion being less than an entirety of the left outer edges and the right outer edges of the front and rear fabric panels;
   a left seam defined by detachably securing the adhesive strips of the left outer edges of the front and rear fabric panels to one another;
   a right seam defined by detachably securing the adhesive strips of the right outer edges of the front and rear fabric panels to one another;
   means for cinching the pair of therapeutic pants disposed along the top edges of the front or rear fabric panel;
   at least one retaining pocket positioned along the rear fabric panel;
   multiple cushions disposed within the at least one retaining pocket,
      wherein the multiple cushions are removable from the at least one retaining pocket,
      wherein the multiple cushions include
         a first cushion configured for elevating a hamstring region of the user, and
         a second cushion configured for elevating a calf region of the user,
      wherein the first cushion is in the form of a right triangular prism having an angled lateral face is configured to cause a knee region of the user to be elevated above the hamstring region of the user, wherein the second cushion is in the form of a cuboid having an upper face is configured to cause the calf region of the user to be substantially aligned with the knee region of the user, and wherein the second cushion has a substantially uniform thickness that corresponds to a maximum thickness of the first cushion; and means for enclosing the multiple cushions within the at least one retaining pocket.

2. The therapeutic pants of claim 1, wherein the means for cinching includes hook-and-loop fasteners, one or more buttons, a zipper, a snap fastener, a magnet, a clip, a drawstring, an elastic band, or any combination thereof.

3. The therapeutic pants of claim 1, wherein the means for enclosing includes hook-and-loop fasteners, one or more buttons, a zipper, a snap fastener, a clip, a magnet, an elastic band, or any combination thereof.

4. The therapeutic pants of claim 3, wherein the at least one retaining pocket is oriented such that when the means for enclosing are disengaged, the at least one retaining pocket opens downward opposite the top edges of the front or rear fabric panel.

5. The therapeutic pants of claim 3, wherein the at least one retaining pocket is oriented such that when the means for enclosing are disengaged, the at least one retaining pocket opens upward toward the top edges of the front or rear fabric panel.

6. The therapeutic pants of claim 3, wherein the at least one retaining pocket is oriented such that when the means for enclosing are disengaged, the at least one retaining pocket opens laterally toward the left seam, the right seam, or either medial side opposite the left or right seam.

7. The therapeutic pants of claim 1, wherein the multiple cushions, a material of the front and rear fabric panels, or both are made of non-allergenic, antimicrobial, or flame-retardant fabric.

8. The therapeutic pants of claim 1, wherein the multiple cushions are made of memory foam, latex, feathers, polyester, silicone or Polyurethane gel, Polystyrene beads, cotton, an air cushion, a natural filling, or any combination thereof.

9. The therapeutic pants of claim 1, wherein the second cushion is between 0.5 and 3 inches thick.

10. The therapeutic pants of claim 1, further comprising:
an elastic front waistband that extends around at least a portion of the front fabric panel; and
an elastic back waistband that extends around at least a portion of the rear fabric panel.

11. The therapeutic pants of claim 1, further comprising:
a left elastic band that extends around at least a portion of a bottom edge of a left leg portion of the front and rear fabric panels; and
a right elastic band that extends around at least a portion of a bottom edge of a right leg portion of the front and rear fabric panels.

12. The therapeutic pants of claim 1, further comprising:
a utility pocket configured for storing personal items or medications and disposed on the front or rear fabric panel,
wherein the utility pocket is oriented such that the utility pocket opens upward toward the top edge of the front or rear fabric panel.

13. The therapeutic pants of claim 9, wherein the second cushion is between 6 and 19 inches in length.

14. The therapeutic pants of claim 8, wherein the first and second cushions are made of different materials.

15. The therapeutic pants of claim 1, wherein each pant leg formed by the front and rear fabric panels tapers to a narrower bottom edge.

16. A pair of pants comprising:
a front fabric panel that includes a top edge, a left outer edge, and a right outer edge,
wherein adhesive strips of hook-and-loop fasteners are disposed along at least a portion of the left and right outer edges of the front fabric panel;
a rear fabric panel that includes a top edge, a left outer edge, and a right outer edge,
wherein adhesive strips of hook-and-loop fasteners are disposed along at least a portion of the left and right outer edges of the rear fabric panel;
a left seam defined by securing the adhesive strips disposed along the left outer edges of the front and rear fabric panels to one another;
a right seam defined by securing the adhesive strips disposed along the right outer edges of the front and rear fabric panels to one another;
at least one pocket positioned along the rear fabric panel;
a first cushion disposed within the at least one pocket,
wherein the first cushion is in the form of a right triangular prism having an angled lateral face is configured to cause a knee region of an individual to be elevated above a hamstring region of the individual; and
a second cushion disposed within the at least one pocket,
wherein the second cushion is in the form of a cuboid having an upper face is configured to cause a calf region of the individual to be substantially aligned with the knee region of the individual;
wherein the second cushion has a substantially uniform thickness that corresponds to a maximum thickness of the first cushion.

17. The pair of pants of claim 16, further comprising:
means enclosing the first and second cushions within the at least one pocket.

18. The pair of pants of claim 16, wherein the at least one pocket includes a first pocket for retaining the first cushion and a second pocket for retaining the second cushion.

* * * * *